(12) United States Patent
Genoud et al.

(10) Patent No.: US 12,196,731 B2
(45) Date of Patent: Jan. 14, 2025

(54) METHOD OF SELECTIVELY CATALYTICALLY OXIDIZING DINITROGEN OXIDE, A METHOD OF DETECTING RADIOCARBON, AN APPARATUS, AND USE OF A NiO CATALYST

(71) Applicant: Teknologian tutkimuskeskus VTT Oy, Espoo (FI)

(72) Inventors: Guillaume Genoud, Espoo (FI); Matti Reinikainen, Espoo (FI); Mari-Leena Koskinen-Soivi, Espoo (FI); Johannes Lehmuskoski, Espoo (FI)

(73) Assignee: Teknologian tutkimuskeskus VTT Oy, Espoo (FI)

( * ) Notice: Subject to any disclaimer, the term of this patent is extended or adjusted under 35 U.S.C. 154(b) by 828 days.

(21) Appl. No.: 17/280,210

(22) PCT Filed: Sep. 24, 2019

(86) PCT No.: PCT/FI2019/050686
§ 371 (c)(1),
(2) Date: Mar. 26, 2021

(87) PCT Pub. No.: WO2020/065133
PCT Pub. Date: Apr. 2, 2020

(65) Prior Publication Data
US 2022/0034858 A1    Feb. 3, 2022

(30) Foreign Application Priority Data

Sep. 26, 2018 (FI) .................................. 20185800

(51) Int. Cl.
*G01N 33/00* (2006.01)
*B01D 53/86* (2006.01)
(Continued)

(52) U.S. Cl.
CPC ..... *G01N 33/0055* (2013.01); *B01D 53/8628* (2013.01); *B01D 53/864* (2013.01);
(Continued)

(58) Field of Classification Search
CPC .............. G01N 33/0055; G01N 21/39; G01N 33/004; G01N 33/225; G01N 2201/0612;
(Continued)

(56) References Cited

U.S. PATENT DOCUMENTS 5,314,673 A * 5/1994 Anseth ................... B01J 23/755
                                              423/239.1
2008/0302133 A1* 12/2008 Saysset .................... F25J 3/067
                                              62/617
(Continued)

FOREIGN PATENT DOCUMENTS

CN      107497436 A      12/2017
CN      108144616 A      6/2018
(Continued)

OTHER PUBLICATIONS

WO 2008/142765 A1, Nitrous Oxide Decomposition Catalyst and Method for Purifying Nitrous Oxide-Containing Gas, May 18, 2007, translated (Year: 2007).*
(Continued)

*Primary Examiner* — Samuel P Siefke
*Assistant Examiner* — Valerie Simmons
(74) *Attorney, Agent, or Firm* — Laine IP Oy; Mark W. Scott

(57) ABSTRACT

A method of selectively catalytically oxidizing dinitrogen oxide present in a gaseous sample, comprising: heating a NiO catalyst to a temperature of at least 250° C.; and bringing the gaseous sample into contact with the heated NiO catalyst to oxidize dinitrogen oxide of the gaseous sample in the presence of the heated NiO catalyst.

9 Claims, 6 Drawing Sheets

(51) Int. Cl.
*B01J 23/44* (2006.01)
*B01J 23/78* (2006.01)
*G01N 21/39* (2006.01)
*G01N 33/22* (2006.01)

(52) U.S. Cl.
CPC .............. *B01J 23/44* (2013.01); *B01J 23/78* (2013.01); *G01N 21/39* (2013.01); *G01N 33/004* (2013.01); *G01N 33/225* (2013.01); *B01D 2255/1023* (2013.01); *B01D 2255/2027* (2013.01); *B01D 2255/20753* (2013.01); *G01N 2021/399* (2013.01); *G01N 2201/0612* (2013.01)

(58) Field of Classification Search
CPC .... G01N 33/22; G01N 21/00; B01D 53/8628; B01D 2255/1023; B01D 2255/2027; B01D 2255/20753; B01D 2257/402; B01D 2257/7025; B01D 2258/06; B01D 53/9413; B01D 59/00; B01J 23/44; B01J 23/78; B01J 21/04; B01J 23/755; B01J 23/892; B01J 35/19; B01J 37/031; Y02C 20/10; Y02C 20/20
See application file for complete search history.

(56) References Cited

U.S. PATENT DOCUMENTS

| 2013/0108536 | A1* | 5/2013 | Sumathipala | ........ B01D 53/864 423/245.1 |
|---|---|---|---|---|
| 2016/0011101 | A1 | 1/2016 | Ognibene et al. | |
| 2020/0033256 | A1* | 1/2020 | Iguchi | ..................... G01J 3/021 |

FOREIGN PATENT DOCUMENTS

| DE | 19817529 A1 | 10/1999 | | |
|---|---|---|---|---|
| GB | 2533398 A | 6/2016 | | |
| JP | 2002214090 A | * | 7/2002 | |
| WO | WO9215824 A1 | | 8/1993 | |
| WO | WO2008142765 A1 | | 11/2008 | |
| WO | WO-2018135619 A1 | * | 7/2018 | .............. G01J 3/021 |

OTHER PUBLICATIONS

Translated JP 2002214090.*
Amano, Characteristics of a simultaneous sampling system for the speciation of atmospheric T and 14C, and its application to surface and soil air, 2002, Journal of Radioanalytical and Nuclear Chemistry, vol. 252, No. 2 (2002) 353-357 (Year: 2002).*
Debbagh Boutarbouch et al: Catalytic conversion of N2O over FeZSM-5 zeolite in the presence of CO and No. Applied Catalysis, B: Environmental, 2004, vol. 54, pp. 115-123.
Fan Yu et al.: Porous NiO nano-sheet as an active and stable catalyst for CH4 deep oxidation. Applied Catalysis A: General, 2015, vol. 507, pp. 109-118.
Fleisher et al: Optical measurement of radiocarbon below unity fraction modem by linear absorption spectroscopy. J. Phys. Chem. Letters, 2017, vol. 8, p. 4550.
Fouladvand et al: Methane Oxidation Over Pd Supported on Ceria-Alumina Under Rich/Lean Cycling Conditions. Topics in Catal, 2016, vol. 56, pp. 410-415.
Galli et al: Spectroscopic detection of radiocarbon dioxide at parts-per-quadrillion sensitivity. Optica, 2016, vol. 3, pp. 385-388.
Genoud et al: Radiocarbon dioxide detection based on cavity ring-down spectroscopy and a quantum cascade laser. Optics Letters, 2015, vol. 40, pp. 1342-1345.
McCartt et al: Measurements of carbon-14 with cavity ring-down spectroscopy. Nucl. Instr. Meth. Phys. Res. B, 2015, vol. 361, p. 277.
Ruszak et al: Selective N2O Removal from the Process Gas of Nitric Acid Plants Over Ceramic 12CaO•7Al2O3 Catalyst. Catalysis Letters, 2008, vol. 126, pp. 72-77.

* cited by examiner

Only NiO-NaOH catalyst

NiO-NaOH and Pd catalysts

METHOD OF SELECTIVELY CATALYTICALLY OXIDIZING DINITROGEN OXIDE, A METHOD OF DETECTING RADIOCARBON, AN APPARATUS, AND USE OF A NiO CATALYST

FIELD

The invention concerns a method of selectively removing trace amounts of $N_2O$ from gaseous samples by using catalytic conversion.

BACKGROUND

Background

Carbon has two stable isotopes and an unstable isotope, carbon-14 also called radiocarbon (C-14). It is present in trace amounts on Earth, with an abundance compared to the main carbon isotope ($^{14}C/^{12}C$) of 1.2 part per trillion (ppt). Radiocarbon is produced from nitrogen by thermal neutrons, either naturally in upper atmosphere or in anthropogenic nuclear reactions, e.g. nuclear power plants or past atmospheric nuclear weapon tests. It then enters the carbon cycle and is present in all modern carbon, while it has decayed to a negligible level in fossil carbon due to its half-life of 5730 years. It is therefore the ideal tracer for discriminating between emissions of fossil origin or biogenic origin, and has numerous applications. It is for instance used to monitor the biofraction in mixed fuels for carbon trade schemes, and to evaluate the contribution of fossil emissions to the global greenhouse gas emissions. C-14 is also commonly used in biomedicine to label organic compounds.

C-14 is also one of the main sources of radioactive gas emissions in nuclear facilities, and regulations require it to be monitored.

In nuclear facilities C-14 can be found in concentrations higher than its natural abundance, typically about 1 ppb to 1 ppm. All parts of nuclear power plants are potential sources for radiocarbon emissions in gaseous form, mostly in the form of carbon dioxide but also in other molecular forms such as methane. In waste repositories, for example, biodegradation of radioactive waste produces $^{14}CO_2$ emissions at levels in the range 10 ppb to 1 ppm. Such levels correspond to activity concentrations in the range 1 to 100 Bq/ml. Long-lived radioisotopes such as radiocarbon are particularly challenging to detect in the context of nuclear facilities.

An accelerator mass spectrometer is the state-of-the-art instrument for radiocarbon detection, while liquid scintillation counting is also extensively used in particular in nuclear facilities. These methods have several drawbacks. They are mainly laboratory-based thus requiring off-site sample analysis, which is a disadvantage when large numbers of samples must be analysed or real-time on-line monitoring is needed.

Radiocarbon detection using laser spectroscopy has on-site on line measurement capabilities, and in the future it can benefit many applications in the fields of nuclear safety, biomedicine, and environmental monitoring. This optical technique relies on the detection of absorption lines of $^{14}CO_2$ by using mid-infrared laser spectroscopy.

$N_2O$ is present in trace amounts (about 330 ppb) in the atmosphere but it has strong absorption lines in the 4.0 to 4.5 microns wavelength region. In laser spectroscopy applications, these absorption lines can interfere with the measurement and thus reduce the sensitivity, in particular in applications that rely on radiocarbon detection in the form of carbon dioxide, because absorption lines in the same wavelength region are used for its detection. Strong $N_2O$ absorption lines are present close to $^{14}CO_2$ absorption lines that are used for radiocarbon detection. It is therefore necessary to remove $N_2O$ in order to achieve the highest possible sensitivity.

Detection of radiocarbon dioxide by infrared laser spectroscopy has been experimented in the prior art:

G. Genoud et al., "Radiocarbon dioxide detection based on cavity ring-down spectroscopy and a quantum cascade laser", Optics Letters 40 (2015) 1342-1345, describes the use of cavity ring-down spectroscopy and a quantum cascade laser for monitoring radiocarbon ($^{14}C$) in carbon dioxide.

McCartt, T. Ognibene, G. Bench, and K. Turteltaub, "Measurements of carbon-14 with cavity ring-down spectroscopy", Nucl. Instr. Meth. Phys. Res. B 361 (2015) 277.

I. Galli et al., "Spectroscopic detection of radiocarbon dioxide at parts-per-quadrillion sensitivity", Optica 3 (2016) 385-388.

A. J. Fleisher, D. A. Long, Q. Liu, L. Gameson, and J. T. Hodges, "Optical measurement of radiocarbon below unity fraction modern by linear absorption spectroscopy", J. Phys. Chem. Letters 8 (2017) 4550.

Various catalysts for converting $N_2O$ have been proposed. Typically, catalytic conversion takes place via a decomposition reaction.

M. Ruszak, et al., "Selective $N_2O$ Removal from the Process Gas of Nitric Acid Plants Over Ceramic $12CaO \cdot 7Al_2O_3$ Catalyst", Catalysis Letters 126 (2008) 72-77, describes catalytic high temperature decomposition (secondary abatement) of nitrous oxide over calcium aluminate $12CaO \cdot 7Al_2O_3$ (mayenite).

M. N. Debbagh Boutarbouch, et al., "Catalytic conversion of $N_2O$ over FeZSM-5 zeolite in the presence of CO and NO", Applied Catalysis, B: Environmental 54 (2004) 115-123, describes the conversion of $N_2O$ in the presence of NO and CO over steam-activated FeZSM-5.

A NiO catalyst was used for oxidation of $CH_4$ by Fan Yu et al., "Porous NiO nano-sheet as an active and stable catalyst for $CH_4$ deep oxidation", Applied Catalysis A: General 507 (2015) 109-118. The concentration of $CH_4$ in the sample was relatively high, about 1%.

There is a need for developing a sensitive method for the detection of radiocarbon in various molecular forms, particularly $^{14}CO_2$ and $^{14}CH_4$.

There is a further need for providing an online and onsite method for monitoring radiocarbon.

The embodiments of the present invention are intended to overcome at least some of the above discussed disadvantages and restrictions of the prior art.

SUMMARY OF THE INVENTION

The invention is defined by the features of the independent claims. Some specific embodiments are defined in the dependent claims.

According to a first aspect of the present invention, there is provided a method of selectively catalytically oxidizing dinitrogen oxide present in a gaseous sample, comprising: heating a NiO catalyst to a temperature of at least 250° C.; and bringing the gaseous sample into contact with the heated NiO catalyst to oxidize dinitrogen oxide of the gaseous sample in the presence of the heated NiO catalyst.

Various embodiments of the first aspect may comprise at least one feature from the following bulleted list:

The concentration of methane in the sample is less than 1% and the oxidation of the dinitrogen oxide is carried out while avoiding oxidation of any methane present in the sample.

The catalyst is a heterogeneous alkaline NiO catalyst.

The catalyst is a heterogeneous NiO/NaOH catalyst.

The catalyst is heated to a temperature of at least 300° C., preferably to a temperature in the range from 350 to 500° C.

The gaseous sample additionally contains $^{14}CO_2$ and $^{14}CH_4$.

The gaseous sample is a gaseous emission sample from a nuclear power plant.

The gaseous sample is a gaseous atmospheric sample.

As a result of the oxidation step, the gaseous sample is adapted for determination of the amount of $^{14}CO_2$ in the gaseous sample by infrared absorption spectroscopy.

According to a second aspect of the present invention, there is provided a method of detecting radiocarbon in the form of $^{14}CO_2$ in a gaseous sample comprising at least $^{14}CO_2$ and $N_2O$, the method comprising: selectively catalytically oxidizing the dinitrogen oxide present in the gaseous sample by the method according to any of claims 1 to 8; and subsequently determining the amount of $^{14}CO_2$ in the gaseous sample by infrared absorption spectroscopy.

Various embodiments of the second aspect may comprise at least one feature from the following bulleted list:

Before the determination step, the gaseous sample is led to a cryogenic trap which has been cooled to a temperature below 195 K, whereby the $^{14}CO_2$ present in the sample solidifies and becomes trapped; releasing the trapped $^{14}CO_2$ by heating the cryogenic trap to a temperature above 195 K.

The determining step comprises measuring an infrared absorption spectrum of a sample released from the cryogenic trap by using a cavity ring-down laser spectroscopy.

The gaseous sample further comprises $^{14}CH_4$, and the method further comprises, before the determination step: catalytically oxidizing the $^{14}CH_4$ to $^{14}CO_2$ by a second catalyst, whereby the $^{14}CO_2$ to be determined in the determination step also comprises $^{14}CO_2$ converted from the $^{14}CH_4$ present in the gaseous sample.

The second catalyst is a Pd catalyst, and the step of catalytically oxidizing the $^{14}CH_4$ to $^{14}CO_2$ comprises: heating the Pd catalyst to a temperature of at least 300° C.; bringing the gaseous sample into contact with the heated Pd catalyst; whereby the heated Pd catalyst catalyses oxidation of the $^{14}CH_4$ present in the gaseous sample to $^{14}CO_2$.

According to a third aspect of the present invention, there is provided an apparatus comprising in a cascade: first means for selectively catalytically oxidizing dinitrogen oxide present in a gaseous sample; and second means for determining the amount of $^{14}CO_2$ present in the gaseous sample by infrared absorption spectroscopy.

Various embodiments of the third aspect may comprise at least one feature from the following bulleted list:

The first means for selectively catalytically oxidizing dinitrogen oxide present in a gaseous sample comprises a first catalyst bed comprising a NiO catalyst.

The apparatus comprises: first means for selectively catalytically oxidizing dinitrogen oxide present in a gaseous sample and further means for catalytically oxidizing $^{14}CH_4$ present in the gaseous sample, in any order; and downstream of said first means and further means: second means for determining the combined amount of $^{14}CO_2$ present in the gaseous sample and $^{14}CO_2$ converted from the $^{14}CH_4$ present in the gaseous sample by infrared absorption spectroscopy.

The further means for catalytically oxidizing $^{14}CH_4$ present in the gaseous sample comprises a second catalyst bed comprising a second catalyst, preferably a Pd catalyst.

The second means comprises a cavity ring-down laser spectrometer comprising a quantum cascade laser as an IR light source.

According to a fourth aspect of the present invention, there is provided use of a NiO catalyst for selectively catalysing oxidation of dinitrogen oxide in a gaseous sample containing $^{14}CO_2$, before detecting the $^{14}CO_2$ by infrared absorption spectroscopy.

Various embodiments of the fourth aspect may comprise at least one feature from the following bulleted list:

The gaseous sample originates from a nuclear power plant.

The gaseous sample is an atmospheric sample.

The gaseous sample is/originates from biofuels, such as biodiesel or biogas.

The present invention provides numerous advantages.

Thus, the present method enables controlled and quantitative removal of $N_2O$ from samples containing carbon dioxide and other carbon compounds.

The present method catalytically converts $N_2O$ without substantially affecting methane concentration and without producing $CO_2$ via undesired side reactions.

Conventional methods cannot differentiate between the different molecular forms of C-14, i.e. different compounds containing C-14. The present method overcomes this drawback.

The present invention provides a sensitive spectroscopic method for detecting radiocarbon in gaseous samples. We have observed that laser spectroscopy can be successfully applied to the monitoring of radiocarbon in various molecular forms.

While the conventional method of liquid scintillation counting for radiocarbon detection relies on detecting emitted radiation, the present invention is based on detecting the underlying molecular species by spectroscopic means. The present invention avoids any interference from other radioactive elements such as tritium.

EMBODIMENTS

Definitions

Figure 1:
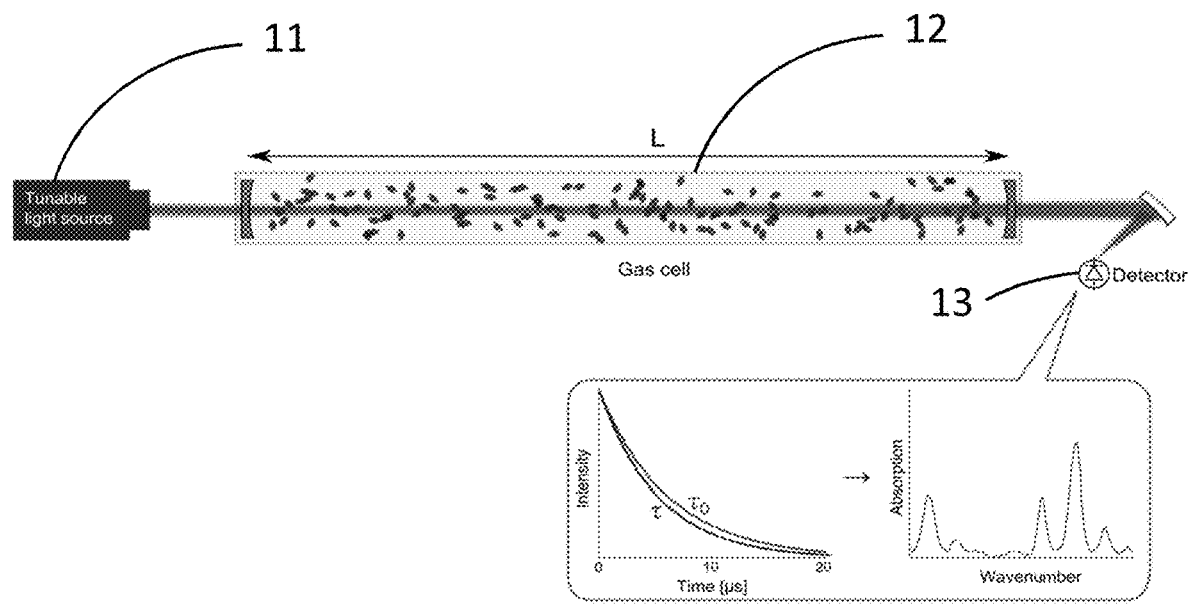
FIG. 1 illustrates schematically a laser spectroscopy apparatus in accordance with at least some embodiments of the present invention.

In the present context, the term "radiocarbon" refers to $^{14}C$, the radioactive isotope of carbon.

In the present context, the term "NiO catalyst" comprises a heterogeneous catalyst comprising nickel oxide.

In the present context, the term "selective catalytic oxidation of $N_2O$" refers to catalytic oxidation of $N_2O$ without affecting the chemical structure of carbonaceous compounds, particularly of methane.

The inventors have surprisingly observed that the interference arising from $N_2O$ in laser spectroscopic radiocarbon detection methods can be successfully eliminated by a catalytic oxidation reaction that is based on using a NiO catalyst. Air samples usually contain trace amounts of $N_2O$, which has strong absorption lines close to the $CO_2$ absorption line in the mid-infrared wavelength range. In the case of detecting $^{12}CO_2$, such trace amounts would not pose any problem, because the levels of $^{12}CO_2$ in the air are in the range 400 ppm to a few %. For the purpose of monitoring ppt levels of $^{14}CO_2$, the interference from $N_2O$ significantly decreases sensitivity.

It is possible to increase the sensitivity by extracting the carbon dioxide from an air sample by using a cryogenic trap. Unfortunately, $N_2O$ also becomes trapped because it has a similar freezing point to that of $CO_2$. Therefore, removal of $N_2O$ before cryogenic trapping, and particularly before the spectroscopic measurement, is required.

The present invention is based on catalytic conversion and removal of $N_2O$ by means of an oxidation reaction for the purpose of increasing the sensitivity of radiocarbon detection from gaseous samples by IR absorption spectroscopy, for example laser spectroscopy.

While traditional radiation detectors rely on the detection of emitted radiation, the method presented here detects the molecules containing the radioisotope C-14 itself. The present method is based on optical methods for the detection of molecules containing radiocarbon.

Radiocarbon is a beta emitter. In the present invention, it is not necessary to chemically separate other beta emitters, such as tritium, beforehand, which is an advantage over traditional radiochemistry methods, such as liquid scintillation counting.

In the present invention, radiocarbon originally present in different molecular forms is detected in the form of carbon dioxide ($^{14}CO_2$).

It was surprisingly observed that a NiO catalyst can remove $N_2O$ by oxidation without oxidising carbonaceous species, such as methane. This therefore allows discriminating between C-14 in different molecular forms.

The invention provides several advantages in terms of size, price, and on-site measurement capabilities. The system presented here enables automated onsite and online monitoring of fugitive radiocarbon emissions in nuclear facilities.

In addition, the present method allows differentiating the different molecular forms of C-14.

$N_2O$ Removal

The invention provides a method for removal of $N_2O$ from the sample before quantifying the amount of $CO_2$ by spectroscopic means, for example by absorbance spectroscopy. $N_2O$ is converted to other molecules using a catalytic conversion reaction and a NiO catalyst. The concentration of $N_2O$ that becomes directed to the spectroscopic measurement cell can be reduced in this way, thus increasing the sensitivity of laser spectroscopy for radiocarbon detection.

In one embodiment, $N_2O$ is catalytically oxidized by a first catalyst, which preferably is a NiO catalyst, according to the following reaction:

$$N_2O+O_2 \rightarrow NO_2 \text{ or } NO \text{ or } N_2O_x, \text{ where } x>2$$

The first catalyst is preferably a NiO catalyst, for example a heterogeneous alkaline NiO catalyst, most preferably a NiO/NaOH catalyst. The first catalyst may comprise or consist of NiO. In some embodiments, any Ni catalyst may be used.

The present NiO catalyst can efficiently and selectively convert or oxidize $N_2O$ without oxidizing carbon compounds, such as methane or carbon monoxide or ash, to carbon dioxide. Such oxidation products of carbon compounds, if produced, would seriously impair accurate detection of the $^{14}CO_2$ originally present in the sample.

We have surprisingly observed that in samples containing relatively low levels (less than 1%, preferably less than 0.5%, more preferably less than 0.1%) of methane, such as air samples, the present NiO catalyst did not convert methane to carbon dioxide.

Preferably at least 80%, more preferably at least 90%, even more preferably at least 99% of any methane present in the gaseous sample remained unaffected (not converted to carbon dioxide) by the present NiO catalyst during the oxidation step.

Preferably, the temperature during the catalytic oxidation of $N_2O$ is in the range from 250 to 600° C., for example from 300 to 450° C. or from 400 to 600° C.

The catalytic reaction proceeds more efficiently at high temperatures, such as at temperatures above 300° C., for example above 350° C.

However, in field measurements it is preferable to use a temperature below 600° C. for practical reasons.

We observed that low flow rates, for example 0.1 to 0.4 l/min (NTP)/gram of catalyst, are preferred during the catalytic oxidation of $N_2O$, as $N_2O$ oxidation is then more efficient.

In some embodiments, the NiO/NaOH catalyst is prepared by the method described in Fan Yu et al., section 2.1.

The invention also provides a method of optical detection of $^{14}CO_2$, and optionally also $^{14}CH_4$, in a gaseous sample. In the method, $N_2O$ is first removed, and subsequently the concentration of $^{14}CO_2$ is determined by an infrared laser spectroscopic method. The $^{14}CO_2$ may be initially present in the sample or it may have been converted from the $^{14}CH_4$ initially present in the sample. Such conversion is done before conducting the optical measurement.

Optionally, $^{14}CH_4$ present in the sample is catalytically converted by using a second catalyst, for example a Pd catalyst, to $^{14}CO_2$ in order to determine the combined amount of radiocarbon originating from $^{14}CO_2$ and $^{14}CH_4$ in the sample. By performing two measurements, one with catalytic conversion of $^{14}CH_4$ and another without the conversion, it is possible to calculate the individual amounts of $^{14}CO_2$ and $^{14}CH_4$.

In the embodiments employing a first catalyst and a second catalyst, two separate catalyst beds are preferably used in series, in either order.

In one embodiment, $CH_4$ is catalytically oxidized to $CO_2$ by a second catalyst according to the following reaction:

$$CH_4+O_2 \rightarrow CO_2$$

The second catalyst is preferably a Pd catalyst, for example an alumina supported Pd catalyst.

In one embodiment, the second catalyst is a Pd catalyst comprising 2 to 3 wt-% Pd.

In some embodiments, the Pd catalyst is prepared by the method described in Fouladvand et al., "Methane Oxidation Over Pd Supported on Ceria-Alumina Under Rich/Lean Cycling Conditions", *Topics in Catal.* (2013) 56:410-415.

Other possible catalysts for catalysing oxidation of $^{14}CH_4$ are precious metals, such as platinum or palladium or rhodium.

During the catalytic oxidation of $^{14}CH_4$ by the second catalyst, the temperature is preferably at least 285° C., more preferably in the range 300 to 500° C., most preferably in the range 300 to 350° C.

Cryogenic Trapping

Preferably, before the optical measurement, $^{14}CO_2$ is extracted from the gaseous sample, such as an atmospheric sample. Extraction can be performed by trapping the $^{14}CO_2$ by means of a cryogenic trap.

In one embodiment, $CO_2$ is trapped in a cryogenic trap that is cooled down to below the freezing point of $CO_2$ (195 K), for example to a temperature in the range 150 to 190 K. By heating the trap to a temperature above 195 K, for example to a temperature in the range 200 to 250 K, almost pure $CO_2$ becomes released and can subsequently be analysed by an optical method. Preferably, water is removed from the sample before leading it to the trap to avoid ice formation and clogging of the trap.

Optical Measurement

In some embodiments, the optical detection is based on measuring infrared absorbance of the sample. The preferred wavenumber range is 2200 to 2250 $cm^{-1}$. The preferred absorption line of $CO_2$ for determining the amount of radiocarbon in the form of $^{14}CO_2$ is situated at 2209.1 $cm^{-1}$.

Preferably, the light source is a tunable laser, for example a quantum cascade laser, or an optical parametric oscillator.

In one embodiment, the optical detection method is a cavity ring-down spectroscopic method, and light is detected by an infrared photovoltaic detector at the output of the cavity.

FIG. 1 illustrates schematically a laser spectroscopy apparatus in accordance with at least some embodiments of the present invention. The apparatus comprises a tunable light source 11, a gas cell 12 in form of a cavity, and a detector 13 at the output of the gas cell. The length L of the gas cell is for example 40 cm. Absorption is measured as a function of wavenumber.

In some embodiments, the spectroscopic set-up described in the publication Genoud et al. and comprising a cavity ring-down spectrometer, a quantum cascade laser and an infrared photovoltaic detector is used.

Figure 2:
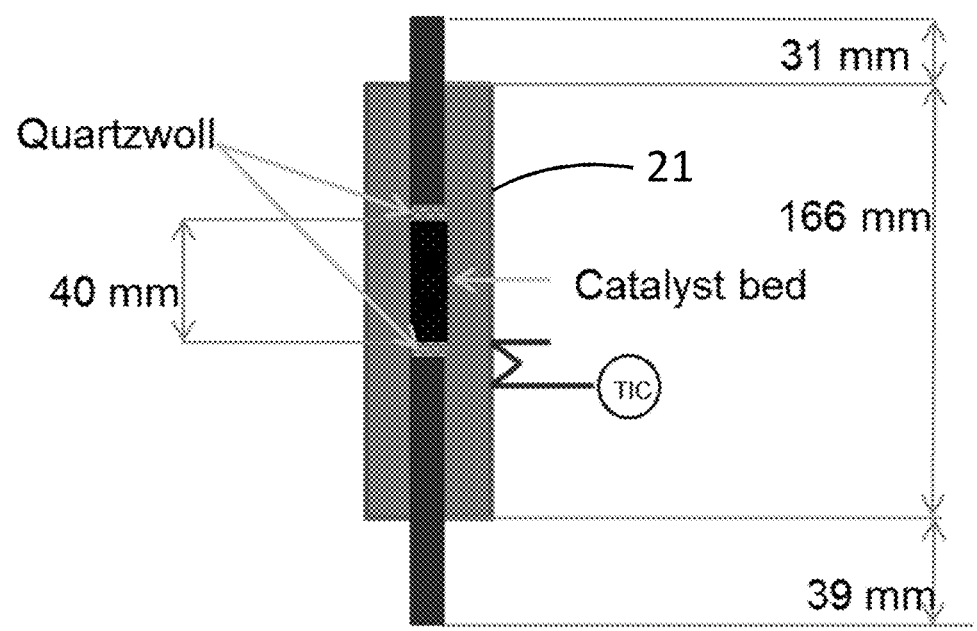
FIG. 2 illustrates schematically a catalyst bed in accordance with at least some embodiments of the present invention.

FIG. 2 illustrates schematically a catalyst bed arrangement comprising a first catalyst in accordance with at least some embodiments of the present invention. The actual catalyst bed 21 has a length of 40 mm. Quartz wool is inserted to both ends of the catalyst bed. TIC refers to a temperature sensor, for example a thermocouple or a thermistor.

The flow rate of the gaseous sample through the catalyst bed is preferably in the range 100 to 500 ml/min (NTP), for example 0.1 to 0.4 l/min (NTP)/gram of catalyst.

Figure 3:
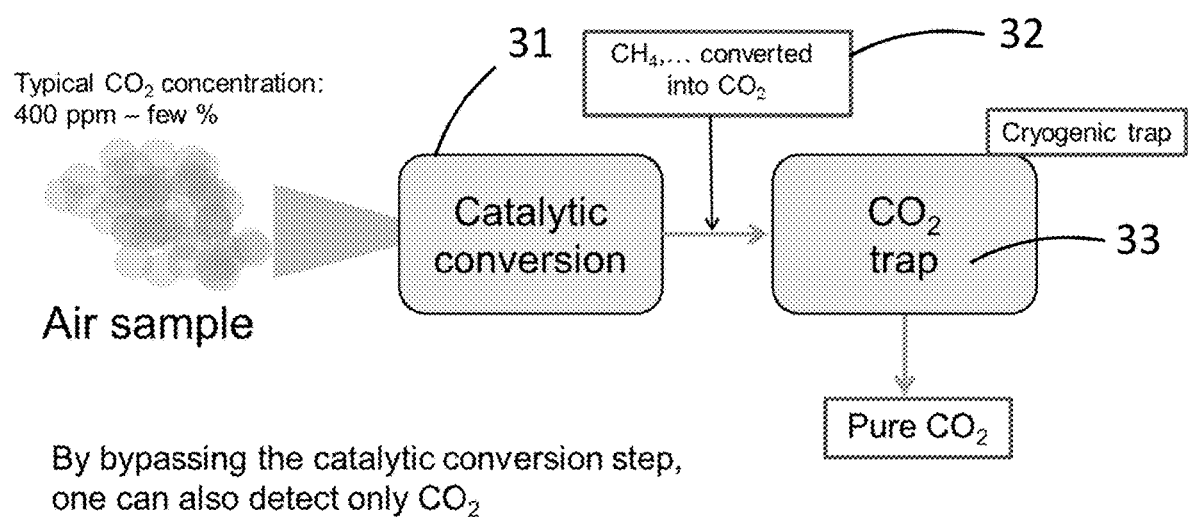
FIG. 3 illustrates schematically a method of extracting $CO_2$ from an air sample in accordance with at least some embodiments of the present invention.

FIG. 3 illustrates schematically a method of extracting $CO_2$ from an air sample in accordance with at least some embodiments of the present invention.

The air sample typically contains 400 ppm to a few % of $CO_2$. The sample is first directed to catalytic conversion 31 of $N_2O$. In this step, the sample is flown through a catalyst bed containing a NiO/NaOH catalyst. Substantially all $N_2O$ becomes oxidized.

Thereafter, optionally, the sample is flown through a second catalyst bed to convert 32 methane quantitatively into carbon dioxide. The second catalyst bed comprises a Pd catalyst.

Next, all $CO_2$ is extracted from the sample in the cryogenic trap 33. During extraction, the trap is in a low temperature (under 195 K). After the extraction step has been completed, the trap is heated to a temperature above 195 K to release pure $CO_2$, which is then directed to spectroscopic analysis (not shown here).

Figure 4:
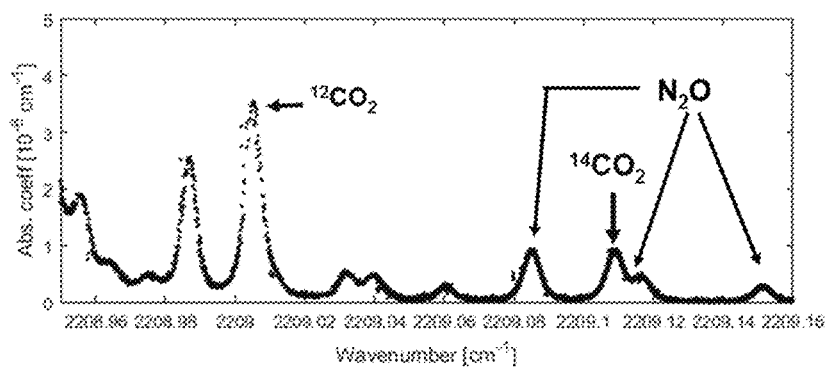
FIG. 4 shows optical spectra measured from gaseous samples treated in accordance with at least some embodiments of the present invention with the cryogenic trap.
Figure 4:
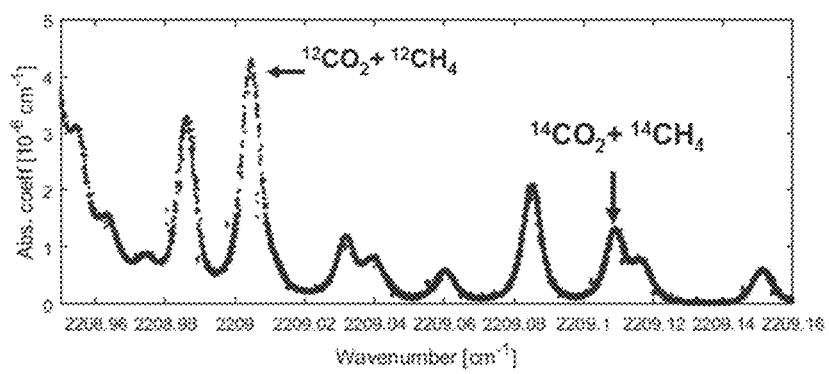

FIG. 4 shows IR absorption spectra measured from gaseous samples treated in accordance with at least some embodiments of the present invention. Carbon dioxide is extracted from air using a cryogenic trap. Almost all $CO_2$ is then sent to the measurement cell. The upper spectrum is measured from a sample from which $N_2O$ was removed by using a NiO/NaOH catalyst. The lower spectrum is measured from a sample from which $N_2O$ was removed by using a NiO/NaOH catalyst and additionally methane was converted to $CO_2$ by using a Pd catalyst. The peak at about 2209.1 $cm^{-1}$ is used for quantifying the initial amounts of $^{14}CO_2$ and $^{14}CH_4$ in the sample. In each graph, the line area of two absorption lines are measured, to give the ratio between the C-14 and C-12 isotopes, which can then be used to determine the amount of radiocarbon in the samples. Together with the data from FIG. 5, the ratio from the upper graph can be used for determining the total amount of $^{14}CO_2$ in the sample, while the ratio from the lower graph can be used for determining the total amount of $^{14}CO_2+^{14}CH_4$ in the samples. 12.15 mbar of almost pure $CO_2$ was in the cell for the measurement of the upper spectrum while 17.6 mbar was used for the measurement of the lower spectrum.

EXAMPLES

Example 1

Preparation of NiO/NaOH Catalyst

As reagents, we used 0.1 mol/l $Ni(NO_3)_2×6H_2O$ and 0.03 mol/l NaOH. Both were aqueous solutions.

The aqueous NaOH solution (0.03 mol/l NaOH) was placed into a dropping funnel. The NaOH solution was dropped to the aqueous Ni solution (0.1 mol/l $Ni(NO_3)_2×6H_2O$) until the pH was 9, as measured by pH-paper. The mixture was stirred by a magnetic stirrer and heated to a temperature of 60° C.

The formed precipitate was filtered by water suction and washed with ion changed water. The precipitate was dried in a heating chamber at 110° C. overnight. The precipitate was calcinated in a rolling calcinator at 550° C. for 4 hours. The catalyst was weighed.

The catalyst was packed into an Inconel tube having an outer diameter of 6 mm, inner diameter of 4 mm, and a length of 25 cm.

No catalyst pretreatment was performed.

Tube heating: In the test conditions with a Ni reactor tube the temperature was 350-550° C.

Catalyst bed length was 3.4 cm, and 0.5 ml of catalyst was added to it. The total flow rate was 100 ml/min (NTP). Quartz wool was placed on both sides of the catalyst bed.

Example 2

Preparation of Pd Catalyst

In the preparation of the Pd/alumina catalyst with 2.2 wt-% Pd, the following reagents were used: as a catalyst carrier Puralox ScFa-200 BI15327, 32.7 ml, and Pd-liquid, 2.25 wt-%, 34.3 ml. The Puralox was weighed to a flask, warmed up to 150° C., vacuum 18 mbar, duration 2 h and cooled to 25° C. The Pd-liquid was impregnated to puralox powder and the flask tapped for 15 minutes. It was left to stabilize overnight. Drying of the product was performed in rotavapor, 80° C., 180 mbar. The dried product was calcined in a rolling calcinator at 550° C. (28° C.-5° C./min-550° C.-1 h). The catalyst was weighed and packed to an Inconel tube having the following dimensions: od 6 mm, id 4 mm, length 23.6 cm. In the test conditions, the Pd-catalyst reactor tube was heated to 350° C. There was no catalyst pretreatment.

Catalyst bed length and volume were optimized as follows: Catalyst (0.5 ml) was packed to the reactor tube. Total flow rate was 100 ml/min. Quartz wool was placed on both sides of the catalyst bed. Pressure with $N_2$ flow was already 1.5 bar. We diluted the catalyst bed. Catalyst was diluted with SiC to prevent over pressure: 0.5 ml catalyst and 0.5 ml SiC no 54. Again the total flow rate was 100 ml/min and quartz wool was placed on both sides of the catalyst bed.

Example 3

Conversion of $N_2O$

The NiO/NaOH catalyst is heated to about 600° C. and the sample gas is flowing through it. As oxygen is naturally present in atmospheric samples, there is no need for additional gas to achieve the oxidation process. $N_2O$ is converted into NO, $NO_2$ or other $N_xO_y$ species, which do not have any interfering absorption lines in the targeted wavelength region.

Example 4

Instrument

The system consists of mainly two parts: a sampling module to extract $CO_2$ from air and to convert methane into carbon dioxide, and a laser spectroscopy module to detect trace amounts of $^{14}CO_2$. The optical detection part is based on the cavity ringdown spectroscopy technique as illustrated in FIG. 1. A quantum cascade laser is used as a light source and coupled to a 40-cm-long cavity composed of high reflectivity mirrors (99.98%). Light is detected by a photovoltaic detector at the output of the cavity. By using these components one can achieve a high sensitivity with a compact setup with a footprint of 45 cm×60 cm. The setup is described in more detail in Genoud et al., where it was characterised using pure $CO_2$.

The sampling module consists of two main parts: a catalytic conversion reactor to convert methane into carbon dioxide, and a cryogenic trap to extract all the $CO_2$ from a gaseous sample. It is possible to differentiate between the two types of radioactive emissions: $^{14}CO_2$ and $^{14}CH_4$. $CO_2$ extraction from air sample is achieved by trapping the $CO_2$ in a trap cooled down to below the freezing point of $CO_2$ (195 K). By heating the trap to above this temperature almost pure $CO_2$ is produced that can then be analysed by using laser spectroscopy. The trap consists of stainless tubing coiled around a copper piece which is cooled down by a cryogenic cooler. The cryogenic cooler is a Brooks PCC Compact Cooler, which is compact and does not require any liquid nitrogen, thus ideal for future in-situ measurements.

Before flowing the sample through the trap, water removal is performed in order to avoid clogging of the trap with ice. Water removal is achieved using a Nafion dryer and magnesium perchlorate.

A cryogenic extraction sequence typically consists of a 30 min period at a low temperature, during which period the sample is flown at a 200 ccm flow rate through the trap. The trap inlet is then closed and the trap is purged for 3 minutes. After the purging, the trap is heated for about 5 minutes to release the frozen $CO_2$. Finally, the trap is cooled down again to start a new cycle. In this way, almost pure (>90%) $CO_2$ is directed into the spectroscopic measurement cell. Once the $CO_2$ has been released, a new cycle starts and the trap is cooled down again. At the same time the previous sample is being measured with laser spectroscopy. When the measurement is completed, the measurement cell is evacuated to vacuum, and the trap is then heated to release the trapped $CO_2$ into the chamber for a next measurement using laser spectroscopy. During the measurement, trapping of a new sample is again initiated with the trap cooling down again.

Catalytic Conversion of Methane and $N_2O$ Removal

Methane present in the sample is converted into $CO_2$ using catalytic conversion. By performing two measurements, with and without catalytic conversion of methane, it is possible to determine the initial amounts of C-14 in the forms of $^{14}CO_2$ and $^{14}CH_4$. A palladium catalyst was used for the catalytic conversion of methane. By operating the reactor above 500° C., conversion efficiency close to 100% was achieved. First, the sample flows through the catalysts, after which it is directed through the water removal section, and finally into the cryogenic trap where all the $CO_2$ (original and converted) freezes.

Using catalytic conversion, methane can be efficiently converted into carbon dioxide, thus allowing quantification of the amounts of C-14 in the forms of $^{14}CO_2$ and $^{14}CH_4$. By using a palladium catalyst, almost complete conversion can be achieved in temperatures above 300° C. This result was confirmed by gas chromatography.

When trapping $CO_2$ using the cryogenic trap, any $N_2O$ present in the sample also becomes trapped, which interferes with the spectroscopic measurement as strong $N_2O$ absorption lines are present close to the targeted $^{14}CO_2$ absorption line. It is therefore necessary to remove the $N_2O$ in order to achieve the highest sensitivity. In the present example, this is performed by using catalytic conversion to oxidise $N_2O$ into $N_2O_x$, with x>2. It was found that a NiO catalyst efficiently converts $N_2O$ without converting methane into $CO_2$. Methane can be converted to $CO_2$ in a controlled manned by using a separate Pd catalyst for that purpose. In this manner, differentiation of these two radiocarbon molecular species, $^{14}CO_2$ and $^{14}CH_4$, is possible.

$N_2O$ removal was found to be linearly dependent on the volume of catalyst. Therefore, a smaller flow rate will result in more efficient $N_2O$ removal. Catalyst temperature also influences $N_2O$ removal: a higher temperature will more efficiently remove $N_2O$.

In this example, the sampling cycle was relatively long for mainly two reasons. The volume and weight of the trap was relatively large resulting in a long time for cooling down and heating. The cavity volume was also larger than necessary, which means that a larger sample volume was required. In order to freeze enough $CO_2$, a longer trapping time was necessary. Finally, in order to achieve optimal $N_2O$ removal, a low flow rate is necessary, which increases the trapping time. The sampling cycle can be shortened by reducing the sampling cell volume, by reducing the weight of the trap and by increasing the amount of catalyst, which will allow increasing the flow rate while maintaining $N_2O$ removal efficiency.

With the current configuration, a complete measurement cycle takes about 1 hour. In the currently used, traditional techniques the sample collection and analysis steps can take several days.

Results

To fully determine the absolute amounts of $^{14}CO_2$ and $^{14}CH_4$ in the sample, 4 different measurements are necessary. First, measurements without $CO_2$ extraction by the cryogenic trap are carried out to determine the total amount of carbon dioxide and methane (the total amount of the main isotope). These measurements are carried out with and without catalytic conversion of $CH_4$. Two absorption lines of $^{12}CO_2$ situated at 2209.93 $cm^{-1}$ and 2209.948 $cm^{-1}$ are used to determine the amount of $CO_2$ in the sample, and the combined amount of $CO_2+CH_4$. This measurement is fast (<1 min) as $CO_2$ trapping is not required.

Another set of measurements is then carried out with the sample flowing through the cryogenic trap where $CO_2$ is extracted. Those measurements are also performed with and without catalytic conversion. The laser is tuned to the wavelength region where the $^{14}CO_2$ line is situated (2209.1 $cm^{-1}$) for these measurements. The line areas of the different targeted absorption lines are then used to determine the concentration of the gaseous species by using the known absorption line strength of the transitions. The measurement itself is fast (typically a few minutes), but the overall analysis time is limited by the trapping time which is relatively long for the moment, as discussed previously.

To test the instrument, a standardised sample was prepared by the National Physical Laboratory (NPL) with elevated amounts of $^{14}CO_2$ and $^{14}CH_4$ in an air matrix. The amounts corresponded to 400 $Bq/m^3$ of $^{14}CO_2$ and 200 $Bq/m^3$ of $^{14}CH_4$, which are typical levels that could be expected from outgassing from nuclear waste.

Figure 5:
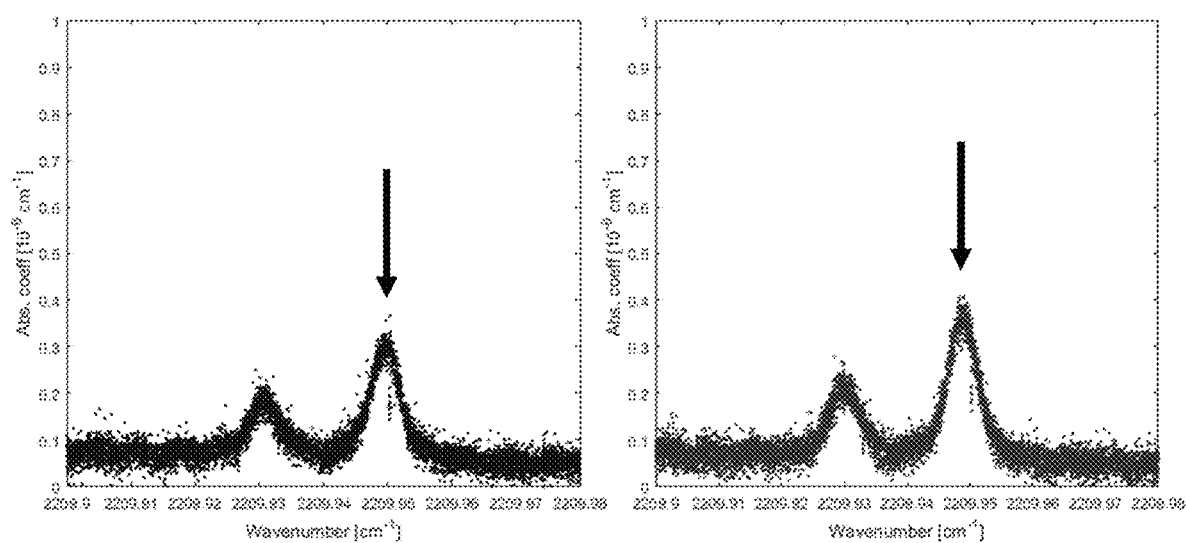
FIG. 5 shows optical spectra measured from gaseous samples treated in accordance with at least some embodiments of the present invention without the cryogenic trap.

The spectra from the measurements that were performed by using the standardised sample are shown in FIGS. 4 and 5. The targeted absorption lines are indicated by arrows. The two measurements without the cryogenic trap (FIG. 5) give the total amount of $CO_2$ and $CO_2+CH_4$ in the samples. After $CO_2$ extraction (FIG. 4), the $^{14}C/^{12}C$ ratio can be determined and the absolute amount of C-14 in carbon dioxide and methane calculated in the following way:

$$^{14}CO_2 = \frac{^{14}C}{^{12}C}N(CO_2) = \frac{A_{14}/S_{14}}{A_{12}/S_{12}} \frac{A_{CO_2}}{S_{CO_2}} \frac{p}{p_0},$$

where A refers to the line areas, S the line strengths, p the sample pressure and p0 the atmospheric pressure. The absorption spectra can be fitted by a sum of Voigt profiles, and the line areas calculated. The amount of $^{14}CO_2$ can then be determined with and without catalytic conversion. This quantity can then be converted to $Bq/m^3$, resulting in about 400 Bq/m3 of $^{14}CO_2$ and 200 Bq/m3 of $^{14}CH_4$. The sensitivity achieved here is thus sufficient for applications in nuclear facilities.

FIG. 5: Spectra recorded without the cryogenic trap. On the left without catalytic conversion and on the right with catalytic conversion. The line area of the absorption line indicated by the arrow in the left spectrum allows determination of the total amount of $CO_2$ in the sample, while the line area of the absorption line indicated by the arrow in the right spectrum allows determination of the total amount of $CO_2+CH_4$ in the samples.

Figure 6:
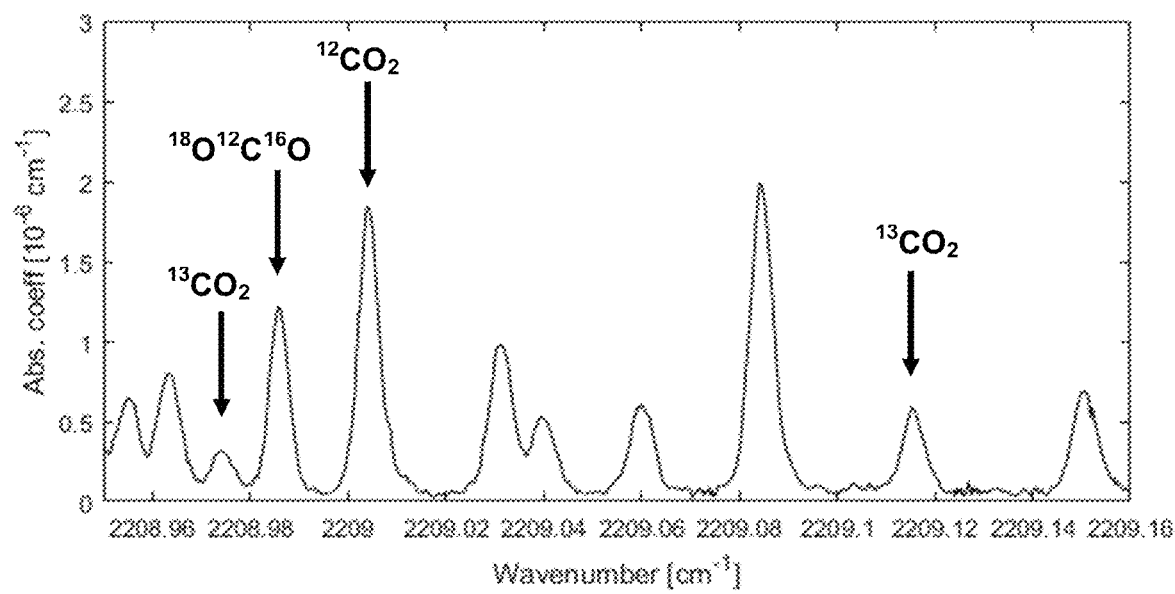
FIG. 6 shows an optical spectrum measured from an ambient air sample.

A comparison measurement was performed by using laboratory air. The results are shown in FIG. 6. As expected, no $^{14}CO_2$ was observed as its natural abundance is only 1.2 ppt, below the detection limit of the instrument used. However, the reduced intensity of the $N_2O$ peaks due to the present method allows determining the stable isotopes $^{12}CO_2$ and $^{13}CO_2$ of carbon dioxide. The sample was circulating through the cryogenic trap for 15 minutes in order to collect a sufficient amount of sample for the measurement, which took about 2 min. The sample pressure in the measurement cell was 5.1 mbar. The recorded spectra are shown in FIG. 6. Stable $CO_2$ isotopes lines are indicated by the arrows. The other lines are $N_2O$ absorption lines. One can see that $CO_2$ lines are of the same levels as the ones seen in FIG. 4, thus showing that the prototype is capable of detecting $CO_2$ isotopes. In an environment with elevated levels of radiocarbon an additional absorption line is present as seen in FIG. 4. Radiocarbon could then easily be detected.

FIG. 6: Spectrum recorded with ambient air. Peaks for different stable isotopes of carbon dioxide are depicted by arrows. However, radiocarbon was present only at its natural abundance of 1.2 ppt and could not be detected.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", i.e. a singular form, throughout this document does not exclude a plurality.

INDUSTRIAL APPLICABILITY

The present invention is industrially applicable at least in the monitoring of radiocarbon gaseous emissions in the form of carbon dioxide and methane from atmospheric samples, typically emitted from nuclear power plants or radioactive waste repositories.

REFERENCE SIGNS LIST 11 tunable light source
12 gas cell
13 detector
21 catalyst bed
31 conversion of $N_2O$
32 conversion of $CH_4$
33 cryogenic trap

CITATION LIST

Non Patent Literature

G. Genoud et al., "Radiocarbon dioxide detection based on cavity ring-down spectroscopy and a quantum cascade laser", *Optics Letters* 40 (2015) 1342-1345.
McCartt, T. Ognibene, G. Bench, and K. Turteltaub, "Measurements of carbon-14 with cavity ring-down spectroscopy", *Nucl. Instr. Meth. Phys. Res. B* 361 (2015) 277.
I. Galli et al., "Spectroscopic detection of radiocarbon dioxide at parts-per-quadrillion sensitivity", *Optica* 3 (2016) 385-388.
A. J. Fleisher, D. A. Long, Q. Liu, L. Gameson, and J. T. Hodges, "Optical measurement of radiocarbon below unity fraction modern by linear absorption spectroscopy", *J. Phys. Chem. Letters* 8 (2017) 4550.
M. Ruszak, et al., "Selective $N_2O$ Removal from the Process Gas of Nitric Acid Plants Over Ceramic $12CaO·7Al_2O_3$ Catalyst", *Catalysis Letters* 126 (2008) 72-77.
M. N. Debbagh Boutarbouch, et al., "Catalytic conversion of $N_2O$ over FeZSM-5 zeolite in the presence of CO and NO", *Applied Catalysis*, B: Environmental 54 (2004) 115-123.
Fan Yu et al., "Porous NiO nano-sheet as an active and stable catalyst for $CH_4$ deep oxidation", *Applied Catalysis A: General* 507 (2015) 109-118.
Fouladvand et al., "Methane Oxidation Over Pd Supported on Ceria-Alumina Under Rich/Lean Cycling Conditions", *Topics in Catal.* (2013) 56:410-415.

The invention claimed is:

1. A method of detecting radiocarbon in the form of $^{14}CO_2$ and $^{14}CH_4$ in a gaseous sample comprising at least $^{14}CO_2$, $^{14}CH_4$, and dinitrogen oxide, the method comprising:
  (a) selectively catalytically oxidizing the dinitrogen oxide present in the gaseous sample with a first catalyst comprising NiO, wherein the first catalyst does not substantially oxidize $^{14}CH_4$ to $^{14}CO_2$ in the gaseous sample;
  (b) catalytically oxidizing $^{14}CH_4$ in the gaseous sample to $^{14}CO_2$ with a second catalyst comprising Pd; and
  (c) determining the amount of $^{14}CO_2$ and $^{14}CH_4$ in the gaseous sample by infrared absorption spectroscopy, wherein the determining step (c) comprises:
    (i) measuring the total amount of $^{14}CO_2$ in a first portion of the gaseous sample and the total amount of $^{14}CO_2$ in a second portion of the gaseous sample by infrared absorption spectroscopy, wherein the total amount of $^{14}CO_2$ measured in the first portion also comprises $^{14}CO_2$ catalytically oxidized from $^{14}CH_4$, and wherein the second portion has not been subjected to catalytically oxidizing of $^{14}CH_4$ to $^{14}CO_2$ with the second catalyst; and
    (ii) from the results of the measuring step (i), determining the amount of $^{14}CO_2$ and $^{14}CH_4$ in the sample.

2. The method according to claim 1, wherein, before the determining step (c):
  the gaseous sample is led to a cryogenic trap which has been cooled to a temperature below 195 K, whereby the $^{14}CO_2$ present in the sample solidifies and becomes trapped; and
  the trapped $^{14}CO_2$ is released by heating the cryogenic trap to a temperature above 195 K.

3. The method according to claim 2, wherein the determining step (c) comprises measuring an infrared absorption spectrum of a sample released from the cryogenic trap by using a cavity ring-down laser spectroscopy.

4. The method according to claim 1, wherein the step of catalytically oxidizing the $^{14}CH_4$ to $^{14}CO_2$ comprises:
  heating the Pd catalyst to a temperature of at least 300° C.; and
  bringing the gaseous sample into contact with the heated Pd catalyst;
  wherein the heated Pd catalyst catalyses oxidation of the $^{14}CH_4$ present in the gaseous sample to $^{14}CO_2$.

5. An apparatus comprising:
  means for selectively catalytically oxidizing dinitrogen oxide present in a gaseous sample with a NiO catalyst, wherein the first catalyst does not substantially oxidize $^{14}CH_4$ to $^{14}CO_2$ in the gaseous sample;
  means for catalytically oxidizing $^{14}CH_4$ in the gaseous sample to $^{14}CO_2$ with a second catalyst comprising Pd; and
  means for determining the amount of $^{14}CO_2$ present in the gaseous sample by infrared absorption spectroscopy, wherein the means for determining is configured to:
    (i) measure the total amount of $^{14}CO_2$ in a first portion of the gaseous sample and the total amount of $^{14}CO_2$ in a second portion of the gaseous sample by infrared absorption spectroscopy, wherein the total amount of $^{14}CO_2$ measured in the first portion also comprises $^{14}CO_2$ catalytically oxidized from $^{14}CH_4$, and wherein the second portion has not been subjected to catalytically oxidizing of $^{14}CH_4$ to $^{14}CO_2$ with the second catalyst; and
(iii) from the results of (i), determine the amount of $^{14}CO_2$ and $^{14}CH_4$ in the sample.

6. The apparatus according to claim 5, wherein the first-means for selectively catalytically oxidizing dinitrogen oxide present in a gaseous sample comprises a first catalyst bed comprising the NiO catalyst.

7. The apparatus according to claim 5, wherein the means for determining comprises a cavity ring-down laser spectrometer comprising a quantum cascade laser as an infrared light source.

8. The method according to claim 1, wherein the determining step (c) further comprises:
(iii) measuring the total amount of $^{14}CO_2$ in a third portion of the gaseous sample and the total amount of $^{14}CO_2$ in a fourth portion of the gaseous sample by infrared absorption spectroscopy, wherein the total amount of $^{14}CO_2$ measured in the third portion also comprises $^{14}CO_2$ catalytically oxidized from $^{14}CH_4$, and wherein the fourth portion has not been subjected to catalytically oxidizing of $^{14}CH_4$ to $^{14}CO_2$ with the second catalyst, and
(iv) from the results of the measuring step (iii), determining the amount of $^{14}CO_2$ and $^{14}CH_4$ in the sample,
wherein the method further comprises subjecting the third portion and the fourth portion to cryogenic trapping to trap the $^{14}CO_2$ in the sample and then releasing the trapped $^{14}CO_2$.

9. A method of detecting radiocarbon in the form of $^{14}CO_2$ and $^{14}CH_4$ in a gaseous sample comprising at least $^{14}CO_2$, $^{14}CH_4$, and dinitrogen oxide, the method comprising:
(i) selectively catalytically oxidizing dinitrogen oxide present in a first portion and a second portion of the gaseous sample with a first catalyst comprising NiO;
(ii) catalytically oxidizing $^{14}CH_4$ in the first portion of the gaseous sample to $^{14}CO_2$ with a second catalyst;
(iii) after steps (i) and (ii), subjecting the first portion and the second portion to cryogenic trapping to trap the $^{14}CO_2$ in the gaseous sample in a cryogenic trap and then releasing the trapped $^{14}CO_2$ from the cryogenic trap;
(iv) measuring the total amount of $^{14}CO_2$ in the first portion of the gaseous sample and the total amount of $^{14}CO_2$ in the second portion of the gaseous sample by infrared absorption spectroscopy; and
(v) from the results of the measuring step (iv), determining the amount of $^{14}CO_2$ and $^{14}CH_4$ in the gaseous sample,
wherein the total amount of $^{14}CO_2$ measured in the first portion also comprises $^{14}CO_2$ catalytically oxidized from $^{14}CH_4$, and
wherein the second portion has not been subjected to catalytically oxidizing of $^{14}CH_4$ to $^{14}CO_2$ with the second catalyst.

* * * * *